United States Patent [19]

Brown, Jr.

[11] Patent Number: 5,350,845

[45] Date of Patent: Sep. 27, 1994

[54] PROCESS FOR PREPARING 7-SUBSTITUTED-AMINO-3-HYDROXY-3-CEPHEM-4-PROTECTED CARBOXY-SULFOXIDE ESTERS

[75] Inventor: Frank Brown, Jr., West Lafayette, Ind.

[73] Assignee: Eli Lilly and Company, Indianapolis, Ind.

[21] Appl. No.: 976,592

[22] Filed: Nov. 13, 1992

Related U.S. Application Data

[63] Continuation-in-part of Ser. No. 866,652, Apr. 8, 1992, abandoned.

[51] Int. Cl.$^5$ ............................................ C07D 501/04
[52] U.S. Cl. .................................. 540/215; 540/222; 540/221
[58] Field of Search ................ 540/215, 222, 221, 228

[56] References Cited

U.S. PATENT DOCUMENTS

| | | | |
|---|---|---|---|
| 3,917,587 | 11/1975 | Chauvette | 260/243 C |
| 4,031,084 | 6/1977 | Kukolja et al. | 260/243 C |
| 4,052,387 | 10/1977 | Kukolja | 544/22 |
| 4,075,203 | 2/1978 | Chou | 544/18 |
| 4,081,440 | 3/1978 | Kukolja | 260/239 A |
| 4,115,643 | 9/1978 | Kukolja et al. | 544/16 |
| 4,190,724 | 2/1980 | Chou | 544/16 |
| 4,289,695 | 9/1981 | Chou | 260/239 A |
| 4,950,753 | 8/1990 | Copp et al. | 540/230 |

OTHER PUBLICATIONS

*Journal of Medicinal Chemistry*, Chemistry of Cephalosporin Antibiotics. 30 3-Methoxy-and 3-Halo-3-cephems; Chauvette and Pennington vol. 18 No. 4 pp. 403-408 (1975).

*J. Org. Chem.*, Kukolja et al.; Synthesis of 3-Hydroxy-, 3-Chloro-, and 3-Methoxy-3-cephems from Penicillins via 4-Dithio-2-azetidinone Intermediates vol. 41 pp. 2276-2278 (1976).

*Chem. Pharm. Bull.*, No. 2; Synthesis of 7β-[(Z)-2-(-2-Amino-4-thiazolyl)-2-methoxyiminoacetamido]-3-cephem-4-carboxylic Acid (Ceftizoxime), a New Semisynthetic Cephalosporin Antibiotic. Kobayashi et al. vol. 36 pp. 582-590 (1988).

*Primary Examiner*—Nicholas S. Rizzo
*Attorney, Agent, or Firm*—Janet T. McClain; James J. Sales; Gerald V. Dahling

[57] ABSTRACT

A process for the conversion of a 4-chlorosulfonyl azetidinone (a) to a 3-hydroxy-3-cephem-sulfoxide ester (d) by subjecting an intermediate comprising a tin containing Lewis acid-type Fiedel-Crafts catalyst and 3-exomethylene cepham to ozonolysis.

18 Claims, No Drawings

PROCESS FOR PREPARING 7-SUBSTITUTED-AMINO-3-HYDROXY-3-CEPHEM-4-PROTECTED CARBOXY-SULFOXIDE ESTERS

This application is a continuation-in-part of application Ser. No. 07/866,652 filed Apr. 8, 1992, now abandoned.

BACKGROUND OF THE INVENTION

This invention relates to a process for the manufacture of intermediates for β-lactam antibiotics. In particular, it relates to an improved process for the manufacture of 7-substituted amino-3-hydroxy-3-cephem-4-protected carboxy sulfoxide esters.

The preparation of 3-exomethylenecepham sulfoxide esters is carried out by the known two-step process which comprises the conversion of a penicillin sulfoxide ester to a chlorosulfinylazetidinone followed by the cyclization of the latter to a 3-exomethylenecepham sulfoxide ester. The penicillin sulfoxide ester is converted to the intermediate chlorosulfinylazetidinone with an N-chloro halogenating agent as described by Kukolja in U.S. Pat. No. 4,165,315. The 4-chlorosulfinyl-azetidinone intermediates are described and claimed by Kukolja in U.S. Pat. No. 4,081,440. Chou, U.S. Pat. No. 4,075,203, describes the preparation of 3-exomethylene-cepham sulfoxide ester via conversion of the penicillin sulfoxide ester in step 1 to the 4-chlorosulfinylazetidinone with an N-chloro halogenating agent in the presence of an alkylene oxide and calcium oxide. Later, Chou, U.S. Pat. No. 4,289,695, describes an improved process for 3-exomethylenecepham sulfoxide esters by employing an acid scavenging cross-linked polyvinylpyridine polymer in step 1.

Kukolja, U.S. Pat. No. 4,052,387, describes the cyclization of 4-chlorosulfinylazetidinones with a Lewis acid-type Friedel-Crafts catalyst, a Bronsted proton acid-type Friedel-Crafts catalyst or with a metathetic cation-forming agent. Subsequently, Chou, U.S. Pat. No. 4,190,724, describes and claims an improved process which comprises carrying out the Kukolja Friedel-Crafts catalyzed cyclization of a 4-chlorosulfinylazetidinone in the presence of oxo compounds such as ethers, ketones or phosphine oxides. Copp et al., U.S. Pat. No. 4,950,753, incorporated herein by reference, describe a further improvement of the Kukolja process which comprises carrying out the Friedel-Crafts cyclization in the presence of both an oxo compound of Chou and an unsaturated compound e.g., an alkene such as 1- or 2-hexene, a non-conjugated alkadiene such as 1,4-hexadiene, a cycloalkene such as cyclohexene, an allene, or a non-conjugated cycloalkadiene such as 1,4-cyclohexadiene.

As taught by Kukolja, U.S. Pat. No. 4,052,387 and also by Chou, U.S. Pat. No. 4,190,724, a tin-containing complex is formed when using a tin-containing catalyst such as stannic chloride. The following illustrates such, and also the further processing applied to form the 3-exomethylenecephemsulfoxide, as taught by Chou:

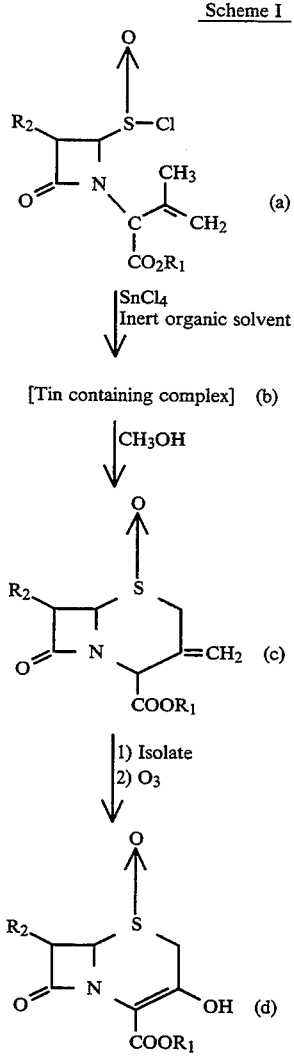

Scheme I ($R_2$ is a protected amino and $R_1$ is a carboxy-protecting group).

In Scheme I, the 4-chlorosulfonylazetidinone (a) is combined with a tin-containing catalyst in an inert organic solvent to form a tin-containing complex intermediate. As noted in Chou U.S. Pat. No. 4,190,724, the complex may be isolated by filtering the reaction mixture, cooled, and stored for further use. An alternative, as shown in Scheme I, includes adding methyl alcohol to the reaction mixture to decompose the complex to provide the corresponding exomethylene cephamsulfoxide (c). Thereafter, as has been taught in the prior art, the 3-exomethylenecepham sulfoxide ester (c) is first isolated and then subjected to ozone to form 3-hydroxy-3-cephem-sulfoxide ester (d). The sulfoxide ester (d) may be reduced by known techniques, such as with phosphorus trichloride or phosphorus tribromide in DMF, to provide the 3-hydroxy-3-cephem ester, a useful intermediate in the production of antibiotics, such as cefaclor.

Heretofore it has been taught that the tin-containing complex had to be decomposed so that isolation of the 3-exomethylene sulfoxide ester could occur before further processing steps, such as ozonolysis, could be taken. However, the present invention affords a novel process which avoids the requirement of isolating the

DESCRIPTION OF THE INVENTION

The process of this invention provides a 3-hydroxy-3-cephem sulfoxide ester represented by the formula 1:

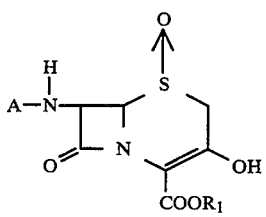
(1)

wherein A is an amino protecting group or a group of the formula

wherein R is the residue of a carboxylic acid RCOOH; and $R_1$ is a carboxy-protecting group, by reacting an intermediate complex comprising a tin-containing Lewis acid-type Friedel-Crafts catalyst and a compound of the formula (2)

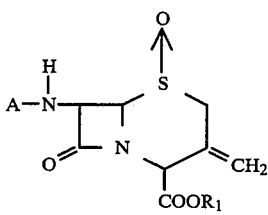
(2)

with ozone, under substantially anhydrous conditions.

As is known in the art, the compound of formula 1 may also exist in the 3-keto tautomeric form, and this tautomer is defined to be encompassed by the formula (1).

The term "residue of a carboxylic acid" includes those 7-position side chains known in the cephalosporin and carbocephalosporin arts, and those 6-position side chains known in the penicillin art. Normally, these side chains are residues of $C_1$-$C_{20}$ carboxylic acids, and are exemplified when R is hydrogen; $C_1$-$C_6$ alkyl, $C_1$-$C_6$ alkyl substituted by cyano, carboxy, halogen, amino, $C_1$-$C_4$ alkoxy, $C_1$-$C_4$ alkylthio, trifluoromethyl, or trifluoro-methylthio; naphthyl, a phenyl or substituted phenyl group of the formula

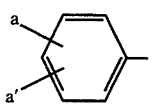

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, $C_1$-$C_4$ alkanoylamino, $C_1$-$C_4$ alkylsulfonylamino, carboxy, carbamoyl, hydroxymethyl, aminomethyl, carboxymethyl, $C_1$-$C_4$ haloalkyl or $C_1$-$C_4$ perhaloalkyl; a group of the formula

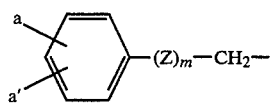

wherein a and a' have the same meanings as defined above, Z is O or S, and m is 0 or 1; an arylmethyl group of the formula

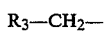

$R_3$—$CH_2$— wherein R is naphthyl, thienyl, furyl, benzothienyl, benzoaminothiazyl, benzofuryl, pyridyl, 4-pyridylthio, pyrimidyl, pyridazinyl, indolyl, pyrazolyl, imidazolyl, triazolyl, tetrazolyl, oxazolyl, thiazolyl, oxadiazolyl, thiadiazolyl, and such aryl groups substituted by amino, hydroxy, halogen, $C_1$-$C_4$ alkyl, $C_1$-$C_4$ alkoxy, phenyl, substituted phenyl, or $C_1$-$C_4$ alkylsulfonylamino; a substituted methyl group of the formula

wherein $R_4$ is cyclohex-1,4-dienyl, a phenyl or substituted phenyl of the formula

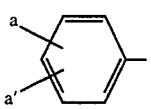

wherein a and a' are as defined above, or $R_4$ is $R_3$ as defined above, and Q is hydroxy, $C_1$-$C_4$ alkanoyloxy, carboxy, sulfo, amino, sulfoamino, or a substituted amino group of the formula

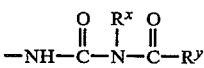

wherein $R^x$ is hydrogen or $C_1$-$C_3$ alkyl, $R^y$ is $C_1$-$C_4$ alkyl, furyl, thienyl, phenyl, halophenyl, nitrophenyl, styryl, halostyryl, nitrostyryl or a group of the formula

wherein $R^x$ has the same meanings as defined above and $R^z$ is hydrogen, $C_1$-$C_3$ alkylsulfonyl, $C_1$-$C_3$ alkyl, or $C_1$-$C_4$ alkanoyl; or Q is a substituted amino group of the formula

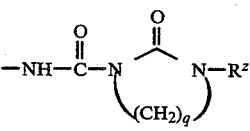

wherein $R^z$ has the same meaning as defined above, and q is 2 or 3; or Q is a substituted amino group of the formula of Q is a benzamido group of the formula

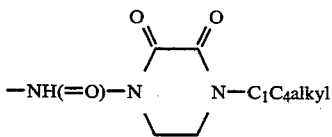

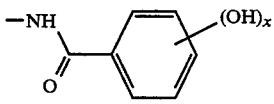

wherein X is 1 to 3;
or Q is a pyridone or hydroxy-substituted pyridonyl-carbonylamino group of the formula

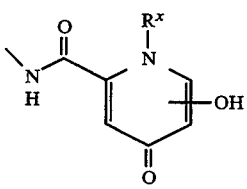

wherein $R^x$ is as defined above;
or Q is a pyridylcarbonylamino group of the formula

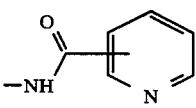

such group optionally substituted by $C_1-C_4$ alkyl, amino, carboxy, hydroxy or halogen; or Q is an imidazolyl or pyrazolyl group of the formula

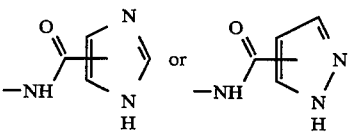

and such imidazolyl or pyrazolyl optionally substituted by $C_1-C_4$ alkyl, carboxy, amino, or halogen; or Q is a benzpyridazin-4-one group or tautomer thereof represented by the formula

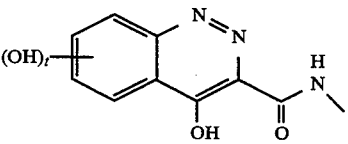
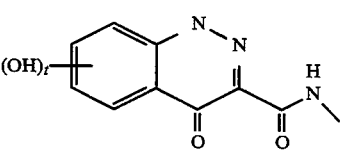

wherein $R^x$ is as defined above, and t is 1 to 3; or Q is a benzpyranone group of the formula

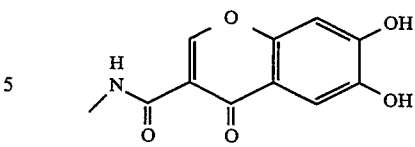

or R is a group of the formula

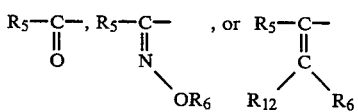

wherein $R_5$ is $R_3$ or $R_4$ as defined above, $R_{12}$ is hydrogen or halogen, and $R_6$ is hydrogen, $C_1-C_4$ alkyl, $C_1-C_4$ alkyl substituted by halogen, a carboxy-substituted alkyl or cycloalkyl group represented by the formula

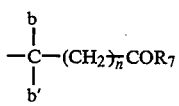

wherein b and b' independently are hydrogen or $C_1-C_3$ alkyl, n is 0, 1, 2, or 3; b and b' when taken together with the carbon to which they are bonded form a 3- to 6-membered carbocyclic ring, and $R_7$ is hydroxy, $C_1-C_4$ amino, $C_1-C_4$ alkylamino, or di($C_1-C_4$ alkyl)amino; or $R_6$ is $C_1-C_4$ substituted by phenyl or phenyl substituted by one or two of the same or different groups selected from among $C_1-C_4$ alkyl, hydroxy, halogen, carboxy or protected carboxy; or $R_6$ is $C_1-C_4$ alkyl substituted by amino or protected amino; or $R_6$ is $C_1-C_4$ alkenyl; or $R_6$ is a cyclic lactam group of the formula

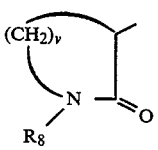

wherein v is 2-4 and $R_8$ is hydrogen or $C_1-C_3$ alkyl; or $R_6$ is an aryl methyl group of the formula

wherein $R_3$ has the same meanings as defined herein above.

The term "carboxy-protecting group+ as used in the specification refers to one of the ester derivatives of a carboxylic acid group commonly employed to block or protect the carboxylic acid group while reactions are carried out on other functional groups on the compound. Examples of such carboxylic acid protecting groups include 4-nitrobenzyl, 4-methylbenzyl, 3,4-dimethoxybenzyl, 2,4-dimethoxybenzyl, 2,4,6-trimethoxybenzyl, 2,4,6-trimethyl-benzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the ring system and can be removed at the appropriate point without disrupting the remainder of the molecule. Similar carboxy-protecting groups used in the cephalosporin, penicillin and peptide arts can also be used to protect carboxy group substituents of the azetidinone. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The related term "protected carboxy" denotes that a carboxy group is substituted with one of the above carboxy-protecting groups. A preferred carboxy-protecting group is p-nitrophenyl.

The term "amino-protecting group" refers to substituents of the amino group commonly employed to block or protect the amino functionality while reacting other functional groups on the compound. Examples of such amino-protecting groups include the formyl group, the trityl group, the phthalimido group, the groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" denotes that an amino is substituted with an amino-protecting group discussed above.

In the above definition of the compounds represented by the formula (1), $C_1$–$C_6$ alkyl refers to the straight and branched chain alkyl groups such as methyl, ethyl, n-propyl, isopropyl, n-butyl, t-butyl, n-pentyl, n-hexyl, 3-methylpentyl, and like alkyl groups; $C_1$–$C_6$ alkyl substituted by cyano refers to cyanomethyl, cyanoethyl, 4-cyanobutyl, and the like; $C_1$–$C_6$ alkyl substituted by carboxy refers to such groups as carboxymethyl, 2-carboxyethyl, 2-carboxypropyl, 4-carboxybutyl, 5-carboxypentyl, and the like; $C_1$–$C_6$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_1$–$C_6$ alkyl substituted by amino refers to such groups as 2-aminoethyl, aminomethyl, 3-aminopropyl and 4-aminobutyl; $C_1$–$C_6$ alkyl substituted by $C_1$–$C_4$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like group; $C_1$–$C_6$ alkyl substituted by $C_1$–$C_4$ alkylthio refers to such groups as for example methylthiomethyl, 2-methylthioethyl, 2-ethylthiopropyl, 4-methylthiobutyl, 5-ethylthiohexyl, 3-t-butylthiopropyl, and like groups; $C_1$–$C_6$ alkyl substituted by trifluoromethyl is exemplified by 2,2,2-trifluoroethyl, 3,3,3-trifluoropropyl, 4,4,4-trifluorobutyl, and the like; and $C_1$–$C_6$ alkyl substituted by trifluoromethylthio refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_1$–$C_6$ alkyl substituted groups.

When in the formula (1) A is a group of the formula

and R is a substituted phenyl group wherein the substituent(s) are represented by a and a', examples of such groups are halophenyl such as 4-chlorophenyl, 3-bromo-phenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylamino such a 3-methylsulfonylamino, 4-methylsulfonylamino, 3,5-(dimethylsulfonylamino)phenyl, 4-n-butylsulfonylaminophenyl, and 3-ethylsulfonylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxyphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

When R is a substituted phenyl group and a' or a is a $C_1$–$C_4$ haloalkyl or $C_1$–$C_4$ perhaloalkyl, examples of such substituents include chloromethyl, iodomethyl, trichloromethyl, trichloroethyl, 2-bromo-2-methylpropyl, chloropropyl, and fluoromethyl.

Examples wherein R is a group represented by the formula

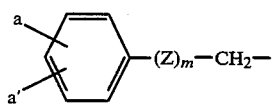

with m=0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=O, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z=S, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples when R is $R_3CH_2-$ wherein $R_3$ is an aryl group are: naphthyl, 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl and benzoaminothiazoyl, and like aryl groups optionally substituted by amino, $C_1$–$C_4$ alkylsulfonylamino, hydroxy, halo, $C_1$–$C_4$ alkyl or $C_1$–$C_4$-alkoxy groups.

Examples wherein R is a substituted methyl group represented by the formula R-CH(Q)- and Q is amino, carboxy, hydroxy, or sulfo, are 2-carboxy-2-phenylacetyl, 2-carboxy-2-(4-hydroxyphenyl)acetyl, 2-amino-2-phenyl-acetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl; and when Q is a substituted amino group represented by the formula

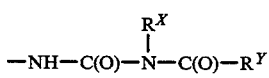

examples of such acyl groups are 2-(N-methyl-N-benzoylcarbamoylamino)-2-phenylacetyl, 2-(N-methyl-N-cinnamoylcarbamoylamino)-2-(2-furyl)acetyl, 2-(N,N-dimethylcarbamoylureido)-2-(4-chlorophenyl)acetyl, 2-[N-methyl-N-(2-chlorocinnamoyl)carbamoylamino]-2-(2-thienyl)-acetyl, and 2-(N-ethyl-N-acetylcarbamoylamino)-2-(4-hydroxyphenyl)acetyl; and when Q is a substituted amino group represented by the formula

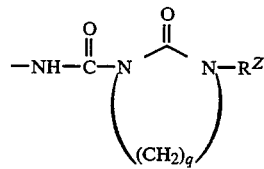

examples are 2-[(3-methylimidazolidin-2-one-1-yl)carbonylamino]-2-phenylacetyl, 2-[(3-acetylimidazolidin-2-one-1-yl)carbonylamino]-2-phenylacetyl, 2-[(3-methylsulfonylimidazolidin-2-one-1-yl)-2-(2-thienyl)acetyl, and 2-[(3-acetylhexahydropyrimidin-2-one-1-yl)carbonylamino]-2-phenylacetyl; and when Q is a hydroxy-substituted benzamido group represented by the formula

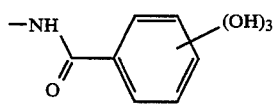

examples of such acyl groups are 2-(2,4-dihydroxybenzamido)-2-phenylacetyl, 2-(4-hydroxybenzamido)-2-(4-hydroxyphenyl)acetyl, 2-(3,4-dihydroxybenzamido)-2-(2-aminothiazol-4-yl)acetyl, 2-(3,5-dihydroxybenzamido)-2-(3-thienyl)acetyl, and 2-(2-hydroxybenzamido)-2-(2-benzofuryl)acetyl.

When Q is an hydroxy-substituted pyridinecarbonylamino group, examples include e.g., 2-hydroxypyridin-4-one-6-ylcarbonylamino and 3-hydroxypyridin-4-one-6-ylcarbonylamino. When Q is a pyridylcarbonylamino group examples are e.g., pyridin-3-ylcarbonylamino, 4-aminopyridin-3-ylcarbonylamino, 5-chloropyridin-2-ylcarbonylamino, 3-carboxypyridin-4-ylcarbonylamino, and 4-aminopyridino-2-ylcarbonylamino. When Q is an imidazole or pyrazole group as defined above examples include e.g., 2-aminoimidazol-4-ylcarbonylamino, 5-carboxy-2-methylimidazol-4-ylcarbonylamino, 5-carboxypyrazol-3-ylcarbonylamino, 3-aminopyrazol-4-ylcarbonylamino and 4-hydroxypyrazol-5-ylcarbonylamino. When Q is a benzpyridazin-4-one-3-ylcarbonylamino group, examples of Q are represented by the formulae

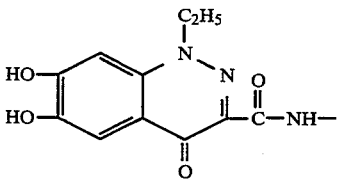

and

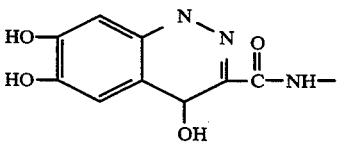

Examples when R is a keto group or an oximino-substituted group represented by the formulae

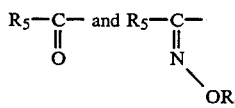

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(2-amino-1,2,4-thiadiazol-4-yl)-2-methoxyiminoacetyl, 2-(2-aminothiazol- 4-yl)-2-methoxy-iminoacetyl, 2-(2-chlorothiazol-4-yl)-2-methoxyiminoacetyl, 2-(2-aminothiazol - 4-yl)-2-(2-carboxyprop-2-yl)oxyiminoacetyl, 2-(2-aminothiazol-4-yl)-2-(2-carbamoyl-prop-2-yl)oxyimino-acetyl, 2-(5-amino-1,3,4-thiadiazol-2-yl)-2-methoxyiminoacetyl, 2-(2-aminothiazol-4-yl)-2-(pyrrolidin-2-one-yl)oxyiminoacetyl, 2-(2-aminothiazol-4-yl)-2-(1-methylpyrrolidin-2-one-3-yl)oxyiminoacetyl, 2-phenyl-2-(pyrrolidin-2-one-3-yl)oxyiminoacetyl, 2-(2-aminooxazol-4-yl)-2-(1-ethylpyrrolidin-2-one-3-yl)oxyiminoacetyl, 2-(2-aminothiazol-4-yl)-2-(1-ethylpiperidin-2-one-3-yl)-2-oxyiminoacetyl, and 2-(2-furyl)-2-(pyrrolidin-2-one-3-yl)oxyiminoacetyl.

Examples when R is a group of the formula

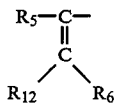

may be found in Hamashima, U.S. Pat. No. 4,634,617, incorporated herein by reference. Exemplary substituents are for $R_{12}$, hydrogen, for $R_5$, phenyl, furyl, thienyl, oxazolyl, isoxazolyl, optionally protected aminoisoxazolyl, thiazolyl, optionally protected aminothiazolyl, thiadiazolyl, and aminothiazolyl, and for $R_6$, $C_1$-$C_3$ alkenyl, especially methylene.

When $R_6$ is $C_1$-$C_4$ alkyl substituted by phenyl or substituted phenyl, such groups are exemplified by benzyl, 4-hydroxybenzyl, 4-chlorobenzyl, 3-carboxybenzyl, 3-chloro-4-hydroxybenzyl, 2-phenylethyl, 1-phenylethyl, 3-phenylpropyl, 4-hydroxy-2-phenylpropyl, 3-phenylbutyl and like phenylalkyl groups.

When $R_6$ represents $C_1$-$C_4$ alkyl substituted by amino or protected amino, examples include 2-aminoethyl, 3-aminopropyl, 4-aminobutyl, 2-aminopropyl and such groups wherein the amino group is protected by an amino-protecting group.

When $R_6$ is a $C_2$-$C_4$ alkenyl group, examples include allyl, butene-2, butene-3, butene-1, and like groups.

Preferred groups for A are those where A is

and R is

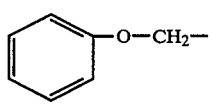

or

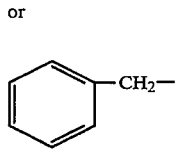

The tin-containing Lewis acid-type Friedel-Crafts catalysts are characterized by the presence of a vacant orbital which can accept an available electron pair, either unshared, e.g. on an oxygen, sulfur, or halide atom, or in a $\pi$ orbital, of a Lewis base-type compound to form a covalent bond. Examples of suitable catalysts are stannic chloride and stannous chloride. Stannic chloride is preferred. The catalyst employed is preferably in an amount of between about 1.0 and 3 moles per mole of sulfinyl chloride (a).

4-Chlorosulfinylazetidinones of formula (a) used in the process are known compounds and, for example, are described by Kukolja in U.S. Pat. No. 4,081,440, incorporated herein by reference. Examples of the starting materials which are used in the process are t-butyl 3-methyl-2-(4-chlorosulfinyl-2-oxo-3-phenylacetylamino-1-azetidinyl)-3-butenoate, t-butyl 3-methyl-2-(4-chlorosulfinyl-2-oxo-3-phenoxyacetylamino-1-azetidinyl)-3-butenoate, diphenylmethyl 3-methyl-2-(4-chlorosulfinyl-2-oxo-3-phenoxyacetylamino-1-azetidinyl)-3-butenoate, p-methoxybenzyl 3-methyl-2-(4-chlorosulfinyl-2-oxo-3-phenylacetylamino-1-azetidinyl)-3-butenoate, p-nitrobenzyl 3-methyl-2-(4-chlorosulfinyl-2-oxo-3-phenoxyacetylamino-1-azetidinyl)-3-butenoate, diphenylmethyl 3-methyl-2-(4-chlorosulfinyl-2-oxo-3-benzoylamino-1-azetidinyl)-3-butenoate, p-nitrobenzyl 3-methyl-2-[4-chlorosulfinyl-2-oxo-3-(-t-butyloxycarbonylamino-phenylacetylamino)-1-azetidinyl]-3-butenoate, benzyl 3-methyl-2-(4-chlorosulfinyl-2-oxo-3-phenoxyacetylamino-1-azetidinyl)-3-butenoate, and benzhydryl 3-methyl-2-(4-chlorosulfinyl-2-oxo-3-acetylamino-1-azetidinyl)-3-butenoate. Preferred azetidinones are represented by formula (a) where A is a group of the formula

R is benzyl, phenoxymethyl, phenylmethyl, or thienylmethyl. A preferred ester group $R_1$ of formula (a) is benzyl or substituted benzyl, especially p-nitrobenzyl.

The cyclization process is carried out at a temperature between about $-15°$ C. and about 60° C. and in an inert organic solvent. Solvents which may be used are described by Kukolja in U.S. Pat. No. 4,052,387, which is incorporated herein by reference and wherein the basic process is described. Solvents include ethyl acetate, the aromatic hydrocarbons such as benzene, toluene, xylene, chlorobenzene and the like, and the halogenated hydrocarbons such as chloroform, methylene chloride, carbon tetrachloride, 1,2-dichloroethane, 1,1,2-trichloroethane, and the like.

As noted above, the cyclization process is carried out under substantially anhydrous conditions. Trace amounts of water are tolerable; however, it is desirable to maintain the reaction mixture in the cyclization process as dry as possible.

The cyclization process may take place in the presence of a nitro compound. The nitro compounds include $C_1$–$C_6$ nitroalkanes and nitro substituted aryls, and are represented by nitromethane, nitroethane, 1-nitropropane, 2-nitropropane, p-nitrotoluene, alpha-nitrotoluene, and nitrobenzene. Nitromethane, 1-nitropropane, nitroethane, and nitrobenzene are preferred. Nitromethane is especially preferred. The nitro compound employed is preferably in the amount of between about 1 and about 4 moles per mole of the sulfinyl halide (a).

In another embodiment, an oxo compound is present during the cyclization. The oxo compounds used in the process are described by Chou, U.S. Pat. No. 4,190,724, which is incorporated herein by reference, and are selected from among the group

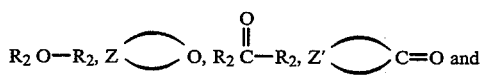

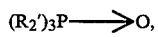

wherein each $R_2$ is independently $C_1$–$C_4$ alkyl; each $R'_2$ is independently $C_1$–$C_4$ alkyl, $C_5$–$C_6$ cycloalkyl, phenyl or phenyl substituted by $C_1$–$C_4$ alkyl, $C_1$–$C_4$ alkoxy, or halogen; Z is —$CH_m$—, —$CH_2$—$CH_2$—O—$CH_2$—$CH_2$—, or —$CH_2$—O—$CH_2CH_2CH_2$—; m is 4 or 5; and Z' is

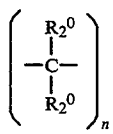

wherein each of $R°_2$ is hydrogen or $C_1$–$C_4$ alkyl, and n is 3 to 6. Preferred oxo compounds are diethyl ether, di-n-propyl ether, acetone and methylethyl ketone. Especially preferred is diethylether. The oxo compound employed in the process is preferably in an amount corresponding to between about 0.75 and about 2 moles per mole of the sulfinyl chloride (a).

In another embodiment, an unsaturated compound is present during the cyclization. The unsaturated compound which can be used in the process may be selected from among $C_2$–$C_{10}$ olefins, $C_5$–$C_{10}$ cycloolefins, non-conjugated $C_5$–$C_{10}$ diolefins, $C_3$–$C_{10}$ allenes, and non-conjugated $C_6$–$C_{10}$ cyclodiolefins. Examples of such alkenes, alkadienes, cycloalkenes, allenes and cyclodienes include, for example, the alkenes ethylene, propylene, 1-butene, 2-butene, 1-pentene, 2-pentene, 1-hexene, 3-hexene, 1-heptene, 3-heptene, 1-octene, 2-nonene, 3-nonene, 1-decene, 5-decene, and like terminal and non-terminal alkenes; non-conjugated alkadienes such as 1,4-pentadiene, 1,4-hexadiene, 3-methyl-1,4-hexadiene, 1,5-hexadiene, 1,5-heptadiene, 1,6-heptadiene, and like dienes; non-conjugated cyclodienes such as 1,4-cyclohexadiene, 1,4-cycloheptadiene, and the like; allenes such as allene, methylallene (1,2-butadiene), dimethylallene (2,3-pentadiene), and the like; cycloalkenes such as cyclopentene, 1-methylcyclo-pent-2-ene, cyclohexene, cycloheptene, cyclooctene, and the like. The alkene, alkadiene or allene may be straight chained or branched and may be substituted with an inert group, preferably on a saturated carbon atom of the alkene.

For example, the unsaturated compound may be substituted with alkyl such as methyl, ethyl or isopropyl; halogen (preferably in a non-allylic position); an esterified carboxy group; an aromatic group such as phenyl or tolyl; nitro; cyano; and alkoxy such as methoxy or ethoxy; and like aprotic substituents which are inert under the conditions of the process.

Non-terminal alkenes may be used in either the cis or trans forms. Preferred unsaturated compounds of the invention are the alkenes, e.g., 1-pentene, 2-pentene, 1-hexene, 2-hexene, 1-heptene, 1-octene and 1-decene; and the cycloalkenes, cyclopentene and cyclohexene. Especially preferred is 1-hexene.

The unsaturated compound employed in the process is preferably present in an amount corresponding to between about one mole to about two moles per mole of sulfinyl chloride (a). An especially preferred amount is between about one mole and about 1.5 mole of unsaturated compound per mole of sulfinyl chloride (a). Best results are achieved with 1 mole of unsaturated compound, expecially 1-hexene, per mole of the compound of formula (a).

In an other embodiment of the cyclization, a 4-chlorosulfinylazetidin-2-one of formula (a) is reacted with between about 1.5 and about 3 moles of stannic chloride per mole of the azetidinone, between about 0.75 and about 2 moles of ethyl ether per mole of the azetidinone, between about 1 and 2 moles of 1-hexene per mole of the azetidinone, and about 1 to 4 moles of nitromethane per mole of the azetidinone, in an inert solvent under substantially anhydrous conditions at a temperature between about −10° C. and about 0° C.

The formation of the complex is carried out generally as follows. The 4-chlorosulfinylazetidinone (a) is dissolved in an anhydrous inert organic solvent. The solution is cooled preferably to a temperature of about 0° C. to about 15° C. The above mentioned compounds may be added to the solution, cooled to about −10° C., and stirred. The catalyst is cooled to about −10° C. and added to the mixture. The solution is stirred under nitrogen and allowed to reach about room temperature (18°-24° C.).

While the complex may be filtered, no further isolation or decomposition of the tin-complex (tin-containing catalyst/3-exo-methylene cepham) need be carried out. The complex formed is then subjected to ozone, in situ. A distinguishing feature of the invention is the obviation of the decompostion or further isolation of the 3-exomethylene cepham from the tin-complex prior to ozonolysis. Therefore, the amount of catalyst is present in a generally stoichiometric amount, or more than just trivial or minute amounts as might be expected after isolation procedures are carried out according to the previously cited references.

Another feature of the invention is the temperature to be used in an ozonolysis, which should be as cold as possible. For current practical production, the temperature range should be about −70° to −5° C., with a temperature range of −70° to −30° C. being preferred. A more preferred temperature range for the ozonlysis is between about −50° to about −35° C. In particular, the temperature used in the in situ ozonolysis is based on the freezing point of the tin-complex/solvent mixture, and the cost related to cooling versus the increase in yield at the lower temperature. As the temperature was lowered for the ozonolysis, surprisingly high yields were obtained. Preferred solvents for the ozonolysis include ethyl acetate and methylene chloride, with ethyl actate being more preferred.

The tin-complex, or tin-containing intermediate, is formed from the addition of a tin-containing catalyst and 4-chlorosulfinylazetidine. The ring-closure or cyclization step has been studied to determine the nature of the tin complex. From the studies thus far indications are that initially a 4-chlorosulfinylazetidine/tin catalyst solid intermediate is formed, and, thereafter, under solid state conditions, the 3-exomethylene cepham sulfoxide/tin catalyst complex is formed. This latter intermediate is, under insitu ozonolysis, transformed to the 3-hydroxy-3-cephem sulfoxide ester/tin complex.

As described herein above and in the Examples, the process affords an effective method for producing 3-hydroxy-3-cephem sulfoxide ester (d) without the need to separate or decompose the complex formed prior to the compound's (d) formation. The 3-hydroxy-3-cephem sulfoxide ester (d) may then be further processed to provide cephalosporin antibiotics. For example, the compound (d) may be reduced to the sulfide, chlorinated at the 3-position, and deesterified all by means known in the art, to produce, for instance, cefaclor.

The following Experimental Section provides further description of the invention but is not to be construed as limitations thereof.

Preparation 1

Methyl 3-Methyl-2-(2-chlorosulfinyl-4-oxo-3-imido-1-azetidinyl)-3-butenoate (refered to herein as sulfinyl chloride)

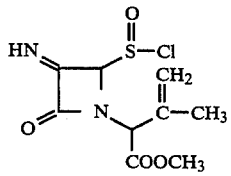

For preparation of the titled product, the process as disclosed in Chou, U.S. Pat. No. 4,190,724 is employed. The product has the following physical data.

H NMR: (CDCl$_3$, 300 MHz, ppm) 1.92 (s, 3H, CH$_3$), 4.50:4.56 (AB, 2H, J=15.1 Hz, side chain CH$_2$), 4.99 (s, 1H, olefinic CH$_2$), 5.06 (s, 1H, CHCOOpNB), 5.22 (d, 1H, J=1.6 Hz, olefinic CH$_2$), 5.25:5.33 (AB, 2H, J=12.9 Hz, pNB CH$_2$), 5.53 (d, 1H, J=4.6 Hz, azetidinone H), 6.27 (dd, 1H, J=4.6 Hz and 10.8 Hz, azetidinone H), 6.90 (dd, 2H, J=7.4 Hz and 8.5 Hz, side chain ArH), 7.01 (t, 1H, J=7.4, side chain ArH), 7.30 (dd, 2H, J=7.4 Hz and 8.5 Hz, side chain ArH), 7.50 (AA'BB', 2H, J=8.9 Hz, pNB ArH), 7.98 (d, 1H, J=10.8 Hz, N-H), 8.23 (AA'BB', 2H, J=8.9 Hz, pNB ArH).

In the following preparations, the intermediate tin complex is formed.

Preparation 2

A 500 ml three-necked round bottomed flask is equipped with a mechanical stirrer, a nitrogen inlet, and a thermometer. The reaction flask is charged with 220 ml of a toluene solution of sulfinyl chloride (25.5 mmoles based on (1B)-6-[(phenoxyacetyl)amino]-penicillanic acid, (4-nitrophenyl)methyl ester-1-oxide. In a separate 50 ml flask is added 10 ml of toluene and diethyl ether [2.5 ml (1.76 g) 23.9 mmoles], and the solution is cooled to 0° to −5° C. Tin (IV) chloride [5.1 ml (11.36 g) 43.6 mmoles] is added to the toluene/diethyl ether solution and the resultant slurry is immediately cooled to 0° C. with an acetone/dry ice bath. The toluene solution of sulfinyl chloride is cooled to 15° C. and the tin (IV) chloride/diethyl ether/toluene slurry is added to the sulfinyl chloride in 5 to 10 seconds using 5 ml of toluene rinse. The resultant slurry is allowed to exotherm to 21° to 23° C. and stir for 18 hours under nitrogen.

Preparation 3

Preparation 2 (above) is repeated except: the toluene solution of sulfinyl chloride is cooled to −50° C. before the 0° C. tin (IV) chloride/diethyl ether/toluene slurry is added.

Preparation 4

Preparation 2 (above) is repeated except: the toluene solution of sulfinyl chloride is cooled to −10° C. before the 0° C. tin (IV) chloride/diethyl ether/toluene slurry was added.

Preparation 5

Preparation 2 (above) is repeated except: no diethyl ether is utilized in the reaction.

Preparation 6

A 500 ml three-necked round bottomed flask is equipped with a mechanical stirrer, a nitrogen inlet, and a thermometer. The reaction flask is charged with 192 ml of a toluene solution of sulfinyl chloride (25.5 mmoles based on (1B)-6-[(phenoxyacetyl)amino]-penicillanic acid, (4-nitrophenyl)methyl ester-1-oxide. In a separate 50 ml flask is added 10 ml of toluene. This toluene is cooled to 0° to −5° C. before tin (IV) chloride [5.1 ml (11.36 g) 43.6 mmoles] is added. The resultant solution is immediately cooled to −10° C. with an acetone/dry ice bath. Nitromethane [3.5 ml (3.94 g) 64.6 mmoles] is added to the sulfinyl chloride solution and the resultant solution is cooled to −10° C. with an acetone/dry ice bath. The tin (IV) chloride/toluene solution is added to the −10° C. sulfinyl chloride solution in 5 to 10 seconds using 5 ml of toluene rinse. The resultant slurry was allowed to exotherm to 21° to 23° C. and stir for four hours under nitrogen.

Preparation 7

Preparation 6 (above) is repeated except: 1-hexene [3.2 ml (2.17 g) 25.8 moles] is also added to the toluene solution of sulfinyl chloride prior to the tin (IV) chloride/toluene addition.

Preparation 8

A 500 ml three-necked round bottomed flask is equipped with a mechanical stirrer, a nitrogen inlet, and a thermometer. The reaction flask is charged with 179 ml of a toluene solution of sulfinyl chloride (24.7 mmoles based on (1B)-6-[(phenoxyacetyl)amino]-penicillanic acid, (4-nitrophenyl) methyl ester-1-oxide). In a separate 50 ml flask is added 10 ml of toluene and diethyl ether [2.4 ml (1.70 g) 22.9 moles], and the solution is cooled to 0° to −5° C. Tin (IV) chloride [4.9 ml (10.91 g) 41.9 mmoles] is added to the toluene/diethyl ether solution and the resultant slurry is immediately cooled to and held at 0° C. with an acetone/dry ice bath. 1-Hexene [3.1 ml (2.10 g) 25.0 mmoles] is added to the sulfinyl chloride solution and the resultant solution is cooled to 10° C. The 0° C. tin (IV) chloride/diethyl ether/toluene slurry is added to the sulfinyl chloride in 5 to 10 seconds using 5 ml of toluene rinse. The resultant slurry is allowed to exotherm to 21° to 23° C. and stir for four hours under nitrogen.

Preparation 9

Preparation 6 (above) is repeated except: diethyl ether [2.5 ml (1.76 g) 23.9 mmoles] is utilized as described in Preparation 2.

Preparation 10

A 500 ml three-necked round bottomed flask is equipped with a mechanical stirrer, a nitrogen inlet, and a thermometer. The reaction flask is charged with 179 ml of a toluene solution of sulfinyl chloride (24.7 mmoles based on (1B)-6-[(phenoxyacetyl)amino]-penicillanic acid, (4-nitrophenyl) methyl ester-1-oxide. In a separate 50 ml flask is added 10 ml of toluene and diethyl ether [2.4 ml (1.70 g) 22.9 mmoles], and the solution is cooled to 0° to −5° C. Tin (IV) chloride [4.9 ml (10.91 g) 41.9 mmoles] was added to the toluene/diethyl ether solution and the resultant slurry is immediately cooled to and held at 0° C. with an acetone/dry ice bath. 1-Hexene [3.1 ml (2.10 g) 25.0 mmoles] and nitromethane [3.3 ml (3.72 g) 60.9 mmoles] are added to the sulfinyl chloride solution and the resultant solution was cooled to 0° C. with an acetone/dry ice bath. The 0° C. tin (IV) chloride/diethyl ether/toluene slurry is added to the 0° C. sulfinyl chloride in 5 to 10 seconds using 5 ml of toluene rinse. The resultant slurry is allowed to exotherm to 21° to 23° C. and stir for four hours under nitrogen.

Preparation 11

Preparation 6 (above) is repeated except: diethyl ether [2.5 ml (1.76 g) 23.9 mmoles] is utilized as described in Preparation 1, and nitrobenzene [6.6 ml (8.21 g) 64.1 mmoles] is used in place of nitromethane. The sulfinyl chloride/tin (IV) chloride/diethyl ether/toluene/nitrobenzene slurry is also only allowed to stir for 90 minutes at 21° to 23° C. rather than four hours.

Preparation 12

Preparation 6 (above) is repeated except: diethyl ether [2.5 ml (1.76 g) 23.9 mmoles] is utilized as described in Preparation 2, and 1-nitropropane [5.7 ml (5.68 g) 63.8 mmoles] is used in place of nitromethane. The sulfinyl chloride/tin (IV) chloride/diethyl ether/toluene/1-nitropropane slurry is also only allowed to stir for 90 minutes at 21° to 23° C. rather than four hours.

Preparation 13

Preparation 6 (above) is repeated except: diethyl ether [2.5 ml (1.76 g) 23.9 mmoles] is utilized as described in Preparation 2, and nitroethane [4.6 ml (4.80 g) 64.0 mmoles] is used in place of nitromethane. The sulfinyl chloride/tin (IV) chloride/diethyl ether/toluene/nitroethane slurry is also only allowed to stir for 90 minutes at 21° to 23° C. rather than four hours.

EXAMPLE 1

7-[(phenoxyacetyl)-amino]-3-hydroxy-3-cephem-4-carboxylic acid, (4-nitrophenyl)methylester, 1-oxide/tin complex To 30 g of 3-exomethylenesulfoxide ester/tin complex is added 250 ml of ethyl acetate. The solution is added into an ozonolysis vessel along with a rinse (using around 50 ml of cold ethyl acetate). The solution is ozonized for 45 minutes after being cooled to −5° C. The resulting mixture (which is a slurry as the product formed is insoluble in ethyl acetate) is analyzed by HPLC. Ozonolysis is continued for another 30 minutes. The resulting mixture is purged with air until it is free from ozone and then 12.5 ml of cold triphenylphosphite (TPP) is added dropwise while maintaining a temperature between 0° and −5° C. The TPP is added over a 38 minute period and then the resulting slurry is stirred for 10 minutes, vacuum filtered, and the filter cake washed with cold ethyl acetate. The cake is dried under vacuum, resulting in 20.96 g of the titled complex.

EXAMPLE 2

7-[(phenoxyacetyl)-amino]-3-hydroxy-3-cephem-4-carboxylic acid, (4-nitrophenyl)methylester, 1-oxide The tin/complex, as prepared by any of preparations 2 through 13, is transferred to an ozonolysis vessel using ethyl acetate at −20° C. While maintaining the temperature between −3° C. and −5° C., the mixture is ozonized for 45 minutes after which it is analyzed for the progress of the reaction by HPLC, then ozonized for an additional 45 minutes. The reaction mixture is analyzed once more by HPLC. The final mixture is then transferred to a separate flask and, after reduction with 25 ml of TPP added over a period of 40 minutes, it is held at 0° C. Methyl alcohol is added and the resulting mixture is stirred for 1 hour at which time 30 ml of deionized water is added and the mixture is stirred for another 15 minutes. An observation is that the 3-exomethylenesulfoxide ester/tin complex is soluble in ethyl acetate which results in a dark brown solution. Upon ozonolysis, the color of the solution changes to a straw yellow color. There was no precipitation observed during ozonolysis or methanolysis.

EXAMPLE 3

7-[(phenoxyacetyl)-amino]-3-hydroxy-3-cephem-4-carboxylic acid, (4-nitrophenyl)methylester/tin complex 3-exomethylenesulfoxide ester/tin complex, as prepared in any of Preparations 2–13, in toluene is stirred for 21 hours and is then cooled to 15° C. and the mother liquor decanted with a gas dispersion tube/vacuum flask apparatus. The wet cake is dissolved in cold ethyl acetate (327 ml) and is transferred to the ozonolysis vessel along with the rinse. Upon cooling the solution to −3° C., the solution is ozonized for 60 minutes. After purging for 10 minutes with air, 16.7 ml of TPP is added dropwise from a dripping funnel over a 35 minute period to result in a homogeneous mixture containing the title compound.

EXAMPLE 4

7-[(phenoxyacetyl)-amino]-3-hydroxy-3-cephem-4-carboxylic acid, (4-nitrophenyl)methyl ester, 1-oxide/tin complex Following a 16 hour stir at approximately 23° C., the tin complex slurry in toluene is cooled to 15° C., and the mother liquor is decanted from the tin slurry using a gas dispersion tube/vacuum flask apparatus. The wet solid is dissolved in 200 ml of ethyl acetate. The solution is then transferred to an ozonolysis vessel equipped with a thermometer and an overhead stirrer while air is passed into the vessel through a bottom valve. The flask is rinsed with 127 ml of ethyl acetate which is added to the ozonolysis vessel resulting in a 12.4% w/v solution. Deionized water (0.5 ml; 0.028 moles with respect to the Pen-V sulfoxide PNB ester) was added to the resultant solution which is stirred while being cooled to −5° C.

With continued stirring, the cold solution is ozonized using a laboratory ozone generator (6 SCFH air and 8 psi) for 45 minutes while the temperature is maintained between −5° and −3° C. The reaction is checked for completeness by HPLC. If the reaction is not essentially complete, ozonolysis is continued. Triphenyl phosphite (16.67 ml) is added dropwise to the reaction mixture over 40 minutes while the temperature was maintained between 0° and 5° C. The reaction mixture is then purged for 10 minutes before it is transferred to a 500 ml Erlenmeyer flask. Dimethylsulfoxide (DMSO) (19.8 ml; 2 molar equivalents with respect to stannic chloride used in the preparation of the tin complex) is added slowly with stirring to the ethyl acetate solution, then the resultant slurry is stirred for an additional 30 minutes. The white solid formed(SnCl4.2DMSO) is filtered, then washed with 50 ml of ethyl acetate prior to drying in vacuo at 50 degrees C. The filtrate is assayed for 3-hydroxycephem sulfoxide ester content by HPLC and a yield of 23–29% was obtained.

EXAMPLE 5

7-[(phenoxyacetyl)-amino]-3-hydroxy-3-ceph-4-carboxylic acid, (4-nitrophenyl)methyl ester, 1-oxide/tin complex Two separate batches of 3-exomethylene-3-cephem sulfoxide/tin complex are used. Both batches are stirred for more than 16 hrs, after which they are cooled to 15° C. and the mother liquor is decanted using a vacuum distillation/gas dispersion tube aparatus. The resulting wet cakes are dissolved in 200 ml of ethyl acetate each.

The first solution is placed in the ozonolysis vessel followed by 0.5 ml deionized water and the mixture is ozonized (6 SCFH and 8 psi) for 45 minutes. The reaction is checked for completeness by HPLC. After cooling the solution to −3° C., the resultant reaction mixture is quenched with 16.67 ml of TPP which is added dropwise over 40 minutes keeping the temperature between 0° and 5° C. The mixture is then purged for 10 minutes, then transferred to a 500 ml Erlenmeyer flask. The mixture is left to stand at 0° C. overnight.

The first solution is transferred to an Erlenmeyer flask and 19.8 ml of DMSO is added slowly while stirring. The resulting slurry is stirred for ½ hour after which the reaction mixture is filtered. The filter cake is washed with 100 ml of fresh ethyl acetate. The beige solid obtained is dried in vacuo at 50° C. The filtrate is concentrated and held at 0° C.

The second solution is transferred to the ozonolysis vessel using 127 ml of ethyl acetate as wash (12.4% w/v). Deionized water (0.5 ml) is added to the solution in the ozonolysis vessel. The resulting mixture is cooled to −3° C. and ozonized (6 SCHF, 8 psi). The reaction mixture is quenched by dropwise addition of 16.67 ml of TPP over a 40 minute period.

The second resultant mixture is washed with three 100 ml aliquots of deionized water. The combined aqueous layers are then back extracted twice with 100 ml of ethyl acetate, then once with 50 ml of ethyl acetate. The organic layers are combined. The resultant solution is divided into 2 portions. Each portion is further washed with 200 ml water. The aqueous layers are back extracted twice with 50 ml of ethyl acetate and combined with the organic layers. Each portion is again washed with 100 ml of water and both organic portions are then combined, stripped of solvent (concentrated) then held at 0° C.

EXAMPLE 6

7-[(phenoxyacetyl)-amino]-3-methylenecephem-4-carboxylic acid, (4-nitrophenyl)methyl ester, 1-oxide/tin complex In a 3-necked, 1-liter round bottomed flask equipped with a mechanical stirrer, thermometer and a nitrogen purge, was added 20.7 g (40 mmoles) of 3-methylene-7-[(phenoxyacetyl)amino]cepham-4-carboxylic acid, (4-nitrophenyl)methyl ester, 1-oxide (I) and 300 ml of methylene chloride. The resultant solution was cooled to 15° C.

To a separate 100 ml round bottomed flask 20 ml of methylene chloride and 4.2 ml of diethyl ether was added and the mixture cooled to 5° C. Tin (IV) chloride (7.96 ml, 68 mmoles) was added to the 5° C. ether solution whereupon a slurry formed on cooling to 0° C. This slurry was added to the rapidly stirring methylene chloride (I) solution and stirring was continued for 30 minutes at 23° C. The solvent was decanted using a gas dispersion tube/vacuum flask apparatus. Hexane (250 ml) was added to the remaining wet cake and the resultant slurry stirred for 90 minutes at room temperature. The slurry was filtered. The filter cake (a white solid) was washed with hexane and dried under vacuum at 23° C. for approximately 16 hours. The yield was 22.97 g. The product melted with decomposition at approximately 139° C. to 161.5° C.

$^1$H NMR: 2.5 ppm (s, DMSO), 3.33 (s, 2H), 3.86 (q, 2H), 4.65 (s, 2H, V (CH$_2$)), 5.11 (d, 1H), 5.35 (s, 2H), 5.42:5.77 (s:s, 1H), 5.54 (s, 1H), 5.85 (dd, 1H), 6.99 (q, 3H), 7.33 (t, 2H), 7.68 (d, 2H), 8.27 (d, 2H), 8.29 (s, 1H). MS: m/z (relative intensity) 500 (19), 475 (4), 365 (4), 333 (14), 309 (12), 192 (16), 155 (72), 151 (43), 135 (43), 119 (103), (60). IR: 3355.60 (NH stretch), 2800–3200 (CH stretch), 1788.24, 1733 and 1680 (C=O stretch). Anal. Calc'd for $C_{23}H_{21}N_3O_8SSnCl_4$: C, 36.35; H, 2.79; N, 5.53; 0, 16.84; S, 4.22; Sn, 15.6; Cl, 18.66. Found: C, 33.74; H, 3.19; N, 4.83; 0, 21.73; S, 3.78; Sn, 15.4; Cl, 17.77.

EXAMPLE 7

{7-(phenoxyacetyl)-amino]-3-hydroxy-3-cephem-4-carboxylic acid, (4-nitrophenyl)methyl ester (II)

The tin/complex (20 g, 26.3 mmoles) prepared in Example 6 was transferred to a 2 liter ozonolysis vessel using 161 ml of ethyl acetate (12.4% w/v solution). While maintaining the temperature between −5° C. and −3° C., the resultant solution was ozonized for 45 minutes and the resultant slurry analyzed by HPLC. The analysis indicated that 10% of (I) was still present. The reaction mixture was ozonized for an additional 30 minutes and analyzed again by HPLC. The analysis indicated that 2% of (I) was present. The slurry was then quenched by the dropwise addition of 25 ml of triphenyl phosphite (TPP) over 40 minutes while maintaining the temperature between 0° C. and 5° C. The reaction was filtered and the wet cake washed with ethyl acetate. The filter cake was dried in vacuo at 50° C. A total of 9.37 g (73.6% purity by HPLC analysis; 52% corrected yield) was obtained. The product melted with decomposition at approximately 148° C. to 155° C.

¹H NMR: 2.50 ppm (s, DMSO), 4.03 (s, 2H), 4.70 (s, 2H, V(CH$_2$)), 5.03 (d, 1H), 5.50 (dd, 2H, PNB(CH$_2$)), 5.93 (q, 1H), 7.0 (q, 3H), 7.34 (t, 2H), 7.77 (d, 2H), 8.13 (d, 1H), 8.27 (d, 2H), 11.18 (s, 1H); MS: m/e (relatively intensity) 502 (1), 4.75 (3), 351 (4), 333 (7), 309 (29), 307 (8), 157 (8), 155 (89), 135 (38), 119 (100) 103 (46); IR: 3307.38 (NH stretch), 2940.85 (CH stretches), 1777.63, 1724.58 and 1679.25 (C=O stretches).

Anal.: C$_{22}$H$_{19}$N$_3$O$_9$S; Calc'd: C, 52.69; H, 3.82; N, 8.38; 0, 28.71; S, 6.93; Found: C, 49.01; H, 3.88; N, 7.67; 0, 28.07; S, 5.76.

EXAMPLE 8

[7-(phenoxyacetyl)-amino]-3-hydroxy-3-cephem-4-carboxylic acid, (4-nitrophenyl) methyl ester (II)

A tin complex was prepared on a 81.7 mmole scale as developed by Chou in U.S. Pat. No. 4,190,724. Following a 19.5 hour stir, the toluene slurry was cooled to 15° C. followed by filtration. The wet cake was dissolved in 200 ml of ethyl acetate and transferred to the ozonolysis vessel using 127 ml of ethyl acetate to rinse (A 12.4% w/v solution with respect to the 1 resulted). The brown solution was cooled to −3° C. and 0.5 ml (27.8 mmoles) of deionized water was added, then the solution was ozonized for 45 minutes. The reaction mixture was analyzed by HPLC after 30 and 45 minutes to determine the extent of the reaction (approximately 45% yield of (II) was formed after 45 minutes). While maintaining the temperature between 0° C. and 5° C., TPP (16.7 ml, 19.7 g; 63.6 mmoles) was added dropwise to the resultant yellow solution over a 40 minute period then the mixture was purged with air for 10 minutes. The white precipitate was filtered. The ethyl acetate solution was analyzed for content of (II). The yield (15.8 g) and percent yield (38.7%) at this point was calculated against a standard using HPLC.

The solution was transferred to an Erlenmeyer flask and 19.8 ml (17.9 g); 279 mmoles of DMSO was added while stirring. The resultant slurry was stirred for 30 minutes then cooled to 0° C. The slurry was filtered, washed with 60 ml of ethyl acetate. The ethyl acetate filtrate was determined by HPLC analysis to contain 14.0 g (34.2% yield) of (II). The white solid was dried in vacuo overnight at 50° C. yielding 56.7 g (97.7% yield) of solid, melting range of 237°–239° C.

EXAMPLE 9

[7-(phenoxyacetyl)-amino-3-hydroxy-3-cephem-4-carboxylic acid, (4-nitrophenyl) methyl ester A tin complex was prepared on a 81.7 mmole scale as developed by Chou in U.S. Pat. No. 4,190,724. After an 18 hour stir, the tin slurry was cooled to 15° C. before transferring the toluene slurry to the ozonolysis vessel using 100 ml of toluene to rinse. Deionized water (0.50 ml, 28 mmoles) was added to the vessel after which the mixture was cooled to −5° C., then ozonized for 60 minutes. The reaction mixture was analyzed by HPLC after 30 and again after 60 minutes. Analysis of the reaction mixture by HPLC indicated that less than 1% of (II) had formed. Ethyl acetate (67 ml) was then added to the reaction mixture and ozonolysis continued for another 2 hours. The progress of the reaction was followed by HPLC - 100, 125, 150 and 180 minutes. Another 100 ml of ethyl acetate was added to the reaction mixture and ozonolysis continued for another hour. The composition of the reaction mixture was determined by HPLC to be 21% (I) and 26.4% (II).

EXAMPLE 10

[7-(phenoxyacetyl)-amino]-3-hydroxy-3-cephem-4-carboxylic acid, (4-nitrophenyl) methyl ester The experiment under Example 8 was repeated, except the mixture was ozonized for 35 minutes. The yield was 48.9%.

EXAMPLE 11

[(Phenoxyacetyl)-amino]-3-hydroxy-3-cephem-4-carboxylic acid, (4-nitrophenyl) methyl ester A tin complex was prepared on a 79.9 mmole scale as developed by Chou in U.S. Pat. No. 4,190,724. Following a 17.25 hour stir, the toluene slurry was cooled to 15° C. followed by filtration. The wet cake was dissolved in 200 ml of ethyl acetate and transferred to the ozonolysis vessel using 127 ml of ethyl acetate to rinse. The brown solution was cooled to −15° C. then the solution was ozonized for 30 minutes. The reaction mixture was analyzed by HPLC after 30 minutes to determine the extent of the reaction (approximately 62% yield of titled product was formed after 30 mintues.) While maintaining the temperature between −5° C. and 0° C., TPP (16.7 mL, 19.7 g; 63.6 mmoles) was added dropwise to the resultant yellow solution over a 40 minute period. The yield (18.9 g) and percent yield (47.1%) at this point was calculated against a standard using HPLC.

The solution was transferred to an Erlenmeyer flask and 19.8 ml (17.9 g); 279 mmoles of DMSO was added while stirring. The resultant slurry was stirred for 30 minutes then cooled to 0° C. The slurry was filtered, washed with 100 ml of ethyl acetate. The ethyl acetate filtrate was determined by HPLC analysis to contain 21.7 g (54.2% yield) of the titled product. The white solid was dried in vacuo overnight at 50° C. yielding 51.2 g (88.2% yield) of solid (SnCl$_4$.2(DMSO)), melting range of 274°–275° C.

EXAMPLE 12

[(Phenoxyacetyl)-amino]-3-hydroxy-3-cephem-4-carboxylic acid, (4-nitrophenyl) methyl ester (2)

A tin complex was prepared on a 79.9 mmole scale as developed by Chou in U.S. Pat. No. 4,190,724. Following a 19.25 hour stir, the toluene slurry was cooled to 15° C. followed by filtration. The wet cake was dissolved in 200 ml of ethyl acetate and transferred to the ozonlysis vessel using 127 ml of ethyl acetate to rinse. The brown solution was cooled to −40° C. then the solution was ozonized for 30 minutes while maintaining the temperature between −40° C. and −36° C. The reaction mixture was analyzed by HPLC after 30 minutes to determine the extent of the reaction (approximately 71% yield of titled product was formed after 30 minutes.) While maintaining the temperature below 0° C., TPP 16.7 mL, (19.7 g; 63.6 mmoles) was added dropwise to the resultant yellow solution over a 40 minute period. The ethyl acetate solution was analyzed for content of titled product. The yield (27.3 g) and percent yield (68.1%) at this point was calculated against a standard using HPLC.

The solution was transferred to an Erlenmeyer flask and 19.8 ml (17.9 g); 279 mmoles of DMSO was added while stirring. The resultant slurry was stirred for 30 minutes then cooled to 0° C. The slurry was filtered, washed with 100 ml of ethyl acetate. The ethyl acetate filtrate was determined by HPLC analysis to contain 29.1 g (72.7% yield) of titled product. The white solid was dried in vacuo overnight at 50° C. yielding 49.3 g (84.9%) of solid (SnCl$_4$.2(DMSO)), melting range of 257.5°–258° C.

We claim:

1. A process for the preparation of a compound of the formula

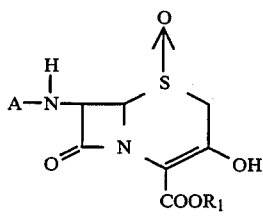

(1)

wherein A is an amino protecting group or a group of the formula

wherein R is the residue of a carboxylic acid RCOOH; and R$_1$ is a carboxy-protecting group, comprising the step of reacting an intermediate complex comprising a tin-containing Lewis acid-type Friedel-Crafts catalyst and a compound of the formula (2)

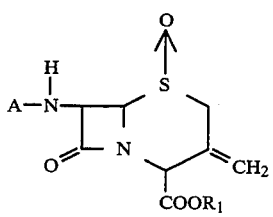

(2)

with ozone, under substantially anhydrous conditions.

2. The process as recited in claim 1 wherein the catalyst is stannic chloride.

3. The process as recited in claim 1 wherein A is of the formula

and R is

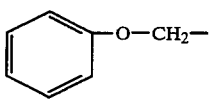

or

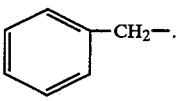

4. The process as recited in claim 1 wherein R$_1$ is 4-nitrobenzyl.

5. The process as recited in claim 1 wherein the ozonolysis takes place in the presence of ethyl acetate or methylene chloride.

6. The process as recited in claim 1 wherein the ozonolysis takes place at a temperature of between about −70° to about −5° C.

7. The process as recited in claim 6 wherein the solvent is ethyl acetate.

8. The process as recited in claim 7 wherein the catalyst is stannic chloride, R$_1$ is p-nitrobenzyl, and A is

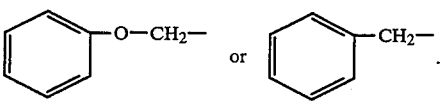

9. The process as recited in claim 1 wherein the ozonolysis takes place at a temperature of between about −50° to about −35° C.

10. The process as recited in claim 1 further comprising reducing the compound of formula (1) to result in a compound of the formula (3).

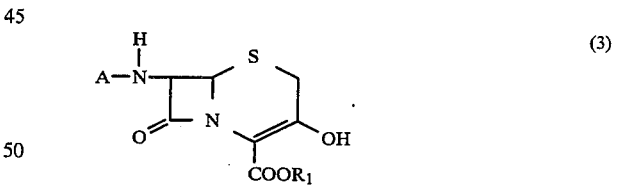

(3)

11. The process as recited in claim 10 further comprising chlorinating the compound of formula (3) to give a compound of the formula (4)

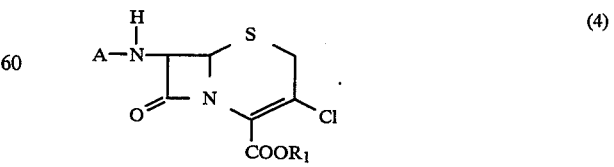

(4)

12. The process as recited in claim 11 further comprising deesterifying the compound of formula (4) to obtain a compound of formula (5)

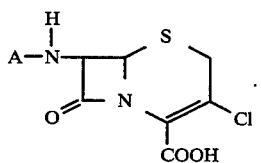

13. The process as recited in claim 12 where A is of the formula

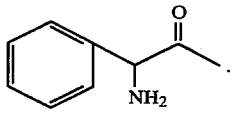

14. In a process for preparing a compound the formula (1)

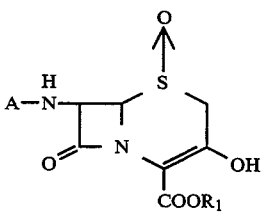   (1)

wherein A is an amino protecting group of the formula

wherein R is the residue of a carboxylic acid RCOOH and $R_1$ is a carboxy protecting group, by reacting a compound of the formula

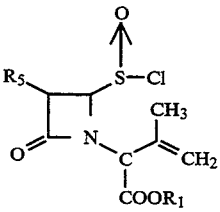

wherein $R_5$ is

or imido, with a tin-containing Lewis acid-type Friedel-Crafts catalyst, said reacting forming an intermediate complex comprising the catalyst and a compound of the formula (2)

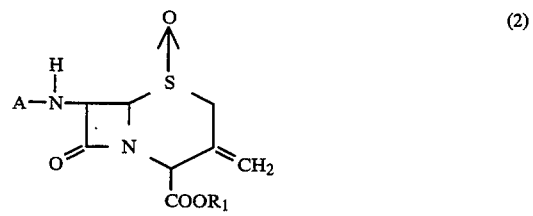   (2)

the improvement characterized in ozonizing the intermediate complex without any substantial prior isolation of the compound of formula (2).

15. The process as recited in claim 14 wherein A is

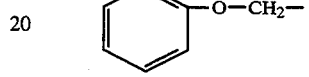

or

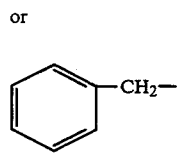

$R_1$ is p-nitrobenzyl; and the catalyst is stannic chloride.

16. The process as recited in claim 14 further comprising reducing the compound of formula (1) to result in a compound of formula (3)

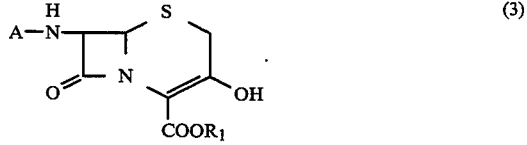   (3)

17. The process as recited in claim 16 further comprising chlorinating the compound of formula (3), and thereafter desterifying the resultant compound to obtain a compound of formula (5)

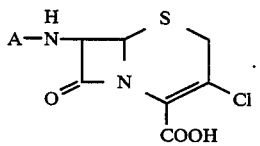

18. The process as recited in claim 14 wherein said ozonolysis takes place in the presence of ethyl acetate, and at a temperature of −50° to −35° C.

* * * * *

UNITED STATES PATENT AND TRADEMARK OFFICE
CERTIFICATE OF CORRECTION

PATENT NO. : 5,350,845
DATED : September 27, 1994
INVENTOR(S) : Frank Brown

It is certified that error appears in the above-indentified patent and that said Letters Patent is hereby corrected as shown below:

On Front Page under Other Publications delete "Intermediates vol. 41", and insert therefor --Intermediates vol. 41 No. 13--.

In column 4, line 14, delete "wherein R", and insert therefor --wherein $R_3$--.

In column 5, line 9, delete "of Q", and insert therefor --or Q--.

In column 5, line 60 insert therefor --or--.

In column 6, line 28, delete "or 3; b and b'", and insert therefor --3; or b and b'--.

In column 6, line 53, delete "group+", and insert therefor --group"--.

In column 12, line 50, delete "R is benzyl", and insert therefor --and R is benzyl--.

In column 13, line 23, delete "$(R_2')_3P \longrightarrow O$", and insert therefor --$(R'_2)_3P \longrightarrow O$--.

UNITED STATES PATENT AND TRADEMARK OFFICE
CERTIFICATE OF CORRECTION

PATENT NO. : 5,350,845
DATED : September 27, 1994
INVENTOR(S) : Frank Brown, Jr.

It is certified that error appears in the above-indentified patent and that said Letters Patent is hereby corrected as shown below:

In column 13, line 29, delete "-$CH_m$", and insert therefor --$(CH)_m$--.

In column 13, lines 32 through 38, delete

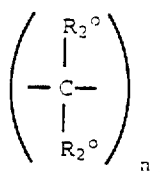

and insert therefor

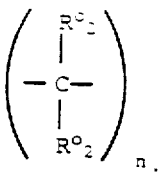

In column 15, line 12, delete "insitu", and insert therefor --in situ--.

In column 16, line 57, delete "22.9 moles", and insert therefor --22.9 mmoles--.

In column 21, line 47, delete "239°C", and insert therefor --239.5°C.

In column 21, line 50, delete "[7-(phenoxyacetyl)-amino-3", and insert therefor --[7-(phenoxyacetyl)-amino]-3--.

In column 25, line 30, delete "group of the formula", and insert therefor --group or a group of the formula--.

UNITED STATES PATENT AND TRADEMARK OFFICE
CERTIFICATE OF CORRECTION

PATENT NO. : 5,350,845
DATED : September 27, 1994
INVENTOR(S) : Frank Brown

It is certified that error appears in the above-indentified patent and that said Letters Patent is hereby corrected as shown below:

In column 25, line 30, delete "group of the formula", and insert therefor --group or a group of the formula--.

Signed and Sealed this

Thirtieth Day of May, 1995

Attest:

BRUCE LEHMAN

Attesting Officer

Commissioner of Patents and Trademarks